United States Patent [19]

Gergely et al.

[11] Patent Number: 4,968,517

[45] Date of Patent: Nov. 6, 1990

[54] METHOD FOR PREPARING AN EFFERVESCENT GRANULATE, AN EFFERVESCENT GRANULATE MADE ACCORDINGLY

[75] Inventors: Gerhard Gergely, Gartengasse 8, A1050 Vienna; Irmgard Gergely; Thomas Gergely, both of Vienna; Ruediger Wolf, Perchtoldsorf, all of Austria

[73] Assignee: Gerhard Gergely, Vienna, Austria

[21] Appl. No.: 221,788

[22] PCT Filed: Oct. 21, 1987

[86] PCT No.: PCT/EP87/00618

§ 371 Date: Aug. 16, 1988

§ 102(e) Date: Aug. 16, 1988

[87] PCT Pub. No.: WO88/02993

PCT Pub. Date: May 5, 1988

[30] Foreign Application Priority Data

Oct. 22, 1986 [DE] Fed. Rep. of Germany ....... 3635864

[51] Int. Cl.$^5$ .............................................. A23P 1/02
[52] U.S. Cl. .................................... 426/285; 426/477; 426/591
[58] Field of Search ..................... 426/591, 285, 477

[56] References Cited

U.S. PATENT DOCUMENTS

| | | | |
|---|---|---|---|
| 2,784,100 | 3/1957 | Endicott | 426/285 |
| 3,359,119 | 4/1967 | Milton . | |
| 3,480,185 | 11/1969 | Steinberg | 426/591 |
| 3,653,914 | 4/1972 | Schmitt | 426/591 |
| 4,362,719 | 12/1982 | Cavazza | 514/4 |
| 4,602,039 | 9/1986 | Cavazza . | |
| 4,687,782 | 8/1987 | Brantman | 514/567 |
| 4,753,804 | 6/1988 | Iaccheri | 426/489 |

FOREIGN PATENT DOCUMENTS

| | | | |
|---|---|---|---|
| 0076340 | 4/1983 | European Pat. Off. | 426/591 |
| 3149517 | 7/1982 | Fed. Rep. of Germany . | |
| 2552308 | 2/1985 | France . | |

*Primary Examiner*—Carolyn Paden
*Attorney, Agent, or Firm*—Hill, Van Santen, Steadman & Simpson

[57] ABSTRACT

The present invention relates to the formation of an effervescent granulate which contains carnitine. The granulate is formed by combining an edible organic acid with an alkaline carbonate or an alkaline earth metal carbonate to form a preliminary reaction solution. After the addition of salt, the crystals are stirred and dried and then finally combined with carnitine.

8 Claims, No Drawings

METHOD FOR PREPARING AN EFFERVESCENT GRANULATE, AN EFFERVESCENT GRANULATE MADE ACCORDINGLY

BACKGROUND OF THE INVENTION

The invention concerns a method for preparing an effervescent granulate including Carnitine an effervescent granulate made accordingly, and its utilization.

The desirable addition of the vitaminlike compound L-Carnitine which plays an important part in the human metabolism, to obtain effervescent granulates, is not practicable due to the high hygroscopicity of this substance, up to the present time. L-Carnitine performs an essential function for the utilization of fatty acids and for the transport of metabolic energy.

The betaine character, that is the formation of an internal salt between the positively charged nitrogen and the negatively charged COO group in Carnitine is the reason for its ability to react on acids and its high hygroscopicity. Therefore, the commercially available pharmaceutical Carnitine preparations mix Carnitine with inert substances in order to prevent the possibilities of reaction. Mainly inert substances have also been suggested for tablet pressing. However, due to the volume it is hardly any longer possible to use large dosages such as for example the oral administration of e.g. 1 g of Carnitine in the form of a tablet. Also a dilution with sugar, carbohydrates and other inert substances for the purpose of establishing a base for preparing a drinking solution results in too large a volume total and too high weights. This base is not acceptable in terms of taste and not economical.

But efforts are made to dissolve these large dosages in water before taking the preparation.

But this modern form of administration designed for larger dosages of active pharmaceutical substances should dissolve fast and in the form of a tasty beverage. However, such preparations require, as is known, an acceptable taste, besides a fast dissolution, due to organic acids of the type of tartaric acid, citric acid, malic acid etc. as well as carbonates or bicarbonates of the type of sodium carbonate, calcium carbonate etc.

When L-Carnitine comes into contact with organic acids, acid salts are formed, as described in the EP-0-0 150 688, which are said to have a by far lower hygroscopicity than L-Carnitine proper. However, these acid salts must now be insulated at this stage, because otherwise they will continue to react with the organic acid finally resulting in a glassy still much more hygroscopic structure than the L-Carnitin proper.

SUMMARY OF THE INVENTION

Therefore, the invention is based on the problem to obtain stable types of administration with organic acids despite the acid activity of L-Carnitine, which must be stable in terms of temperature, and have little hygroscopy, but dissolve fast in water.

DESCRIPTION OF THE PREFERRED EMBODIMENTS

According to the invention this problem is solved by the method of manufacture of effervescent granulates which includes the steps of preparing: a preliminary solution with organic acid, alkaline earth or alkaline earth metal carbonate and solvent; applying the preliminary solution onto organic acid crystals; applying a salt onto the acid crystals which have been moistened with the preliminary reactive solution; adding a pulverized coating; drying the coated crystals and adding L-Carnitine. The foregoing method is an improvement over the process described in German Pat. Application No. P 36 27 475.5-41.

Other specific features of this invention include the use of citric acid as the organic acid, the use of vacuum in the method, the use of a solvent in the preparation of the preliminary solution which is either alcohol or water, the use of anhydrous sodium carbonate as the alkaline metal carbonate, the adding of L-Carnitine in the amount of 15-30 percent by weight with the amount of 20-25 percent being preferred, the utilization of the granulate, preparing an effervescent beverage or in the use of preparing effervescent tablet.

Through the passivation of the surface of the organic acid crystals proposed by the invention it is possible to prevent their influence on the L-Carnitine while the additional drying function of the outer layer of the acid crystals equipped with a coating, counter-acts the hygroscopicity of L-Carnitine. In this manner fast soluble mixtures or tablets are obtained where the action of the organic acid on L-Carnitine is eliminated and which, in addition, are stable in terms of temperature, and have little hygroscopicity.

Here it is of particular advantage to apply anhydrous sodium carbonate onto a crystal surface of citric acid, in a very finely pulverized form. If, for example, a buffer solution of mono-calcium citrate is used in concentrated form, then it is possible to bond large amounts of anhydrous sodium carbonate to the surface of the citric acid crystals without the sodium carbonate being able to take up crystal water. On the one hand, the incorporation of crystal water in the sodium carbonate takes a long time, on the other hand the incorporation of crystal water is impaired by the concentrated solution of mono-calcium citrate.

Thus it is possible to obtain particles by way of a buffer granulation of the surfaces of citric acid crystals and subsequent application of anhydrous sodium carbonate, which show an external alkaline reaction also during the pressing of tablets, but dissolve vigorously upon contact with water.

Surprisingly, mixtures of such a granulate with L-Carnitine are hardly hygroscopical any longer and they dissolve rapidly and clearly in water both in the form of a concentrated granulate and in the form of effervescent tablets. The method of the invention has now made it possible for the first time to make effervescent granulates or tablets which dissolve with a resulting final pH between 4 and 5, which can be stained, can be provided with aromas and sweetening agents, and make it possible to accommodate for instance 1 g of L-Carnitine in a total amount of approximately 4 to 5 g of a granulate or a tablet in line with market conditions and in economical manner. In this way it is possible to use the much cheaper L-Carnitine proper directly, without using the indirect way via acid salts or similar, and to incorporate it under the method of the invention in the likewise cheaper instant complexes which can be utilized in economical manner.

The criteria of the invention disclosed in the foregoing description and in the claims can be essential both individually and in any random combination for the realization of the invention in its various manners of implementation.

We claim:

1. A method for the manufacture of effervescent granulate by the steps of:
   (A) preparing a preliminary reaction solution by:
      (1) providing at least one solid crystal line, edible organic acid;
      (2) providing at least one alkaline carbonate or alkaline earth metal carbonate;
      (3) dissolving and reacting organic acid crystal and alkaline carbonate or alkaline earth metal carbonate in a solvent so as to form a preliminary reaction solution;
   (B) applying the preliminary reactions solution onto organic acid crystals whereby a first bonding layer is formed adhering to the crystals;
   (C) applying a salt which is able to bond water in an irreversible manner in an overall complex onto the acid crystals moistened with the preliminary reactive solution
   (D) thereafter adding a solid pulverized coating mass by intensive stirring to the previously coated crystals;
   (E) drying the coated crystals; and
   (F) adding L-Carnitine to the coated crystals.

2. Method according to claim 8 characterized in that anhydrous sodium carbonate is applied in very finely pulverized form onto the acid crystals moistened with the solution of the preliminary reaction.

3. Method according to claim 1 or 2 characterized in that the L-Carnitine is added in such an amount that the effervescent granulate contains 15-30 weight % L-Carnitine.

4. Method according to claim 3 characterized in that the L-Carnitine is added in such an amount that the effervescent granulate contains 20-25 % L-Carnitine.

5. A method as in claim 1, wherein the organic acid is a citric acid.

6. A method as in claim 1, wherein the coating, drying and/or adding steps of subparagraphs (B), (C), (D), (E) and/or (F) are performed in a vacuum.

7. A method as in claim 1, wherein the solvent subparagraph (A) (3) is at least one member selected from water and alcohol.

8. Effervescent granulate made according to one of the preceding claims.

* * * * *